United States Patent
Cardoso de Vasconcelos et al.

(10) Patent No.: US 9,566,244 B2
(45) Date of Patent: *Feb. 14, 2017

(54) PHARMACEUTICAL COMPOSITION COMPRISING LICARBAZEPINE ACETATE

(71) Applicant: BIAL—Portela & C.A., S.A., S. Mamede do Coronado (PT)

(72) Inventors: Teófilo Cardoso de Vasconcelos, S. Mamede do Coronado (PT); Ricardo Jorge dos Santos Lima, S. Mamede do Coronado (PT); Rui Cerdeira de Campos Costa, S. Mamede do Coronado (PT)

(73) Assignee: BIAL-PORTELE & CA, S.A., S. Mamede do Coronado (PT)

( * ) Notice: Subject to any disclaimer, the term of this patent is extended or adjusted under 35 U.S.C. 154(b) by 0 days.

This patent is subject to a terminal disclaimer.

(21) Appl. No.: 14/108,615

(22) Filed: Dec. 17, 2013

(65) Prior Publication Data

US 2014/0343043 A1 Nov. 20, 2014

Related U.S. Application Data

(63) Continuation of application No. 13/754,439, filed on Jan. 30, 2013, now abandoned, which is a continuation of application No. 12/257,240, filed on Oct. 23, 2008, now Pat. No. 8,372,431.

(60) Provisional application No. 60/982,790, filed on Oct. 26, 2007.

(51) Int. Cl.
| | | |
|---|---|---|
| A61K 31/55 | (2006.01) | |
| A61K 9/16 | (2006.01) | |
| A61K 9/20 | (2006.01) | |
| A61K 47/32 | (2006.01) | |
| A61K 9/00 | (2006.01) | |

(52) U.S. Cl.
CPC ........... *A61K 9/2095* (2013.01); *A61K 9/0056* (2013.01); *A61K 9/1682* (2013.01); *A61K 9/2027* (2013.01); *A61K 9/2054* (2013.01); *A61K 31/55* (2013.01)

(58) Field of Classification Search
None
See application file for complete search history.

(56) References Cited

U.S. PATENT DOCUMENTS

| | | |
|---|---|---|
| 5,326,570 A | 7/1994 | Rudnic et al. |
| 5,753,646 A | 5/1998 | Benés et al. |
| 5,912,013 A | 6/1999 | Rudnic et al. |
| 6,296,873 B1 | 10/2001 | Katzhendler et al. |
| 6,410,054 B1 | 6/2002 | Thosar et al. |
| 6,458,770 B1 | 10/2002 | Van Hoogevest |
| 6,475,510 B1 | 11/2002 | Venkatesh et al. |
| 6,534,090 B2 | 3/2003 | Puthli et al. |
| 7,119,197 B2 | 10/2006 | Learmonth |
| 7,189,846 B2 | 3/2007 | Learmonth |
| 7,241,886 B2 | 7/2007 | Learmonth |
| 7,667,075 B2 | 2/2010 | Dominguez et al. |
| 7,834,177 B2 | 11/2010 | Learmonth et al. |
| 8,372,431 B2 | 2/2013 | Cardoso de Vasconcelos et al. |
| 2003/0175353 A1 | 9/2003 | Dudhara et al. |
| 2004/0087642 A1 | 5/2004 | Zeldis et al. |
| 2004/0142033 A1 | 7/2004 | Franke et al. |
| 2005/0202088 A1 | 9/2005 | Hanshermann et al. |
| 2006/0252745 A1 | 11/2006 | Almeida et al. |
| 2006/0252746 A1 | 11/2006 | Almeida et al. |
| 2007/0071819 A1 | 3/2007 | Kesarwani et al. |
| 2007/0196396 A1 | 8/2007 | Pilgaonkar et al. |
| 2007/0196488 A1 | 8/2007 | Kalb et al. |
| 2008/0081930 A1 | 4/2008 | Dominguez et al. |
| 2008/0139807 A1 | 6/2008 | Learmonth et al. |
| 2011/0319388 A1 | 12/2011 | de Almeida et al. |

FOREIGN PATENT DOCUMENTS

| | | |
|---|---|---|
| EP | 1787642 A1 | 5/2007 |
| EP | 1815849 A1 | 8/2007 |
| EP | 1929997 A1 | 6/2008 |
| JP | 2007529564 A | 10/2007 |
| JP | A-2007 529564 | 10/2007 |
| UZ | 2327 C | 8/2003 |
| WO | WO 9529665 | 11/1995 |
| WO | WO 9835681 A1 | 8/1998 |
| WO | WO 00/32189 | 6/2000 |
| WO | WO 2004004723 A1 | 1/2004 |
| WO | WO 2004026314 A1 | 4/2004 |
| WO | WO 2004035041 A1 | 4/2004 |
| WO | WO 2005092290 A1 | 10/2005 |

(Continued)

OTHER PUBLICATIONS

Parada, António, and Patrício Soares-da-Silva. "The novel anticonvulsant BIA 2-093 inhibits transmitter release during opening of voltage-gated sodium channels: a comparison with carbamazepine and oxcarbazepine." Neurochemistry international 40.5 (2002): 435-440.*
Ambrósio, António F., et al. "Neurotoxic/neuroprotective profile of carbamazepine, oxcarbazepine and two new putative antiepileptic drugs, BIA 2-093 and BIA 2-024." European journal of pharmacology 406.2 (2000): 191-201.*
CAS Registry No. 298-46-4 (Nov. 16, 1984).*
United States Pharmacopeia, Monograph <711> Dissolution (USP, 2005).*
European Pharmacopoeia 5.0, Section 2.9.3. Dissolution Test for Solid Dosage Forms (Ph. Eur. 5, 2005).*
Ansel, et al., "Pharmaceutical Dosage Forms and Drug Delivery Systems," 6th Ed., 1995, pp. 192-203.

(Continued)

*Primary Examiner* — Bethany Barham
*Assistant Examiner* — Peter Anthopolos
(74) *Attorney, Agent, or Firm* — Finnegan, Henderson, Farabow, Garrett & Dunner, LLP.

(57) ABSTRACT

A pharmaceutical composition comprising licarbazepine acetate, especially eslicarbazepine acetate, in combination with suitable excipients, in particular a binder, and a disintegrant. Also disclosed is a granulation process, especially a wet granulation process, for making the pharmaceutical composition.

5 Claims, No Drawings

(56) References Cited

FOREIGN PATENT DOCUMENTS

| WO | WO 2005092294 A1 | 10/2005 |
|---|---|---|
| WO | WO 2006005951 A1 | 1/2006 |
| WO | WO 2006/121363 A1 | 11/2006 |
| WO | WO 2006120501 A1 | 11/2006 |
| WO | WO 2007008576 A1 | 1/2007 |
| WO | WO 2007012793 A1 | 2/2007 |
| WO | WO 2007029093 A1 | 3/2007 |
| WO | WO 2007089926 A1 | 8/2007 |
| WO | WO 2007094694 A1 | 8/2007 |
| WO | WO 2007117166 A1 | 10/2007 |
| WO | WO 2008037044 A1 | 4/2008 |
| WO | WO 2009054743 A1 | 4/2009 |

OTHER PUBLICATIONS

Aerosill® Pharma, Evonik Industries, Product Information, downloaded Jun. 9, 2012, 1 page.
Beringer, Paul, et al., "Remington, The Science and Practice of Pharmacy," Part 5: Pharmaceutical Manufacturing, 21st Edition, pp. 932-933 plus 3 pages cover and publishing information, 2005, Lippincott Williams & Wilkins.
BIAL marketing data sheet entitled "Eslicarbazepine acetate (BIA 2-093) relative bioavailability and bioequivalence of 50 mg/mL oral suspension and 200 mg and 800 mg tablet formulations," 2005, 1 page.
Bühler, Volker, "Polyvinylpyrrolidone Excipients for Pharmaceuticals," 4 pages cover, publishing information, contents, 2005, pp. 5-124 plus 5 pages cover, publishing information and contents, Springer-Verlag Berlin Heidelberg.
Bühler, Volker, "Polyvinylpyrrolidone Excipients for Pharmaceuticals," 2005, pp. 66-78 and 113, Springer-Verlag Berlin Heidelberg.
CAS Registry No. 236295-14-5, Sep. 1, 1999, 3 pages.
"CHMP Assessment Report for Zebinix," Doc. Ref.: EMEA/304525/2009, Feb. 19, 2009, 80 pages, European Medicines Agency, London, UK.
Danish Patent and Trademark Office "State of the art search," Ref. No. SE 2008 02502, Aug. 29, 2008, 8 pages.
Filing receipt and specification for provisional patent application entitled "Composition," by Teófilo Cardoso de Vasconcelos, et al., filed Oct. 26, 2007, as U.S. Appl. No. 60/982,790.
Flesch, G., et al., "Oxcarbazepine final market image tablet formulation bioequivalence study after single administration and at steady state in healthy subjects," International Journal of Clinical Pharmacology and Therapeutics, 2002, vol. 40, No. 11, pp. 524-532.
Fontes-Ribeiro, Carlos, et al., "Eslicarbazepine acetate (BIA 2-093) relative bioavailability and bioequivalence of 50 mg/mL oral suspension and 200mg and 800mg tablet formulations," Drugs R D, 2005, vol. 6, No. 5, pp. 253-260, Adis Data Information BV.
Foreign Communication—Examination Report, European Application No. 08842368.6, Jun. 5, 2013, 7 pages.
Foreign communication from a related counterpart application—First Chinese Office Action translation dated May 20, 2011, CN200880112983.0, 11 pages.
Foreign communication from a related counterpart application—Israeli Office Action translation dated Jul. 11, 2012, IL205160, 2 pages.
Foreign Communication from a related counterpart application—Japanese Office Action with transiation, JP Application No. 2010-530951, Jul. 2, 2013, 7 pages.
Foreign communication from a related counterpart application—Mexican Translation of Key Points of Office Action dated Jun. 27, 2012, MX/a/2010/004323, 1 page.
Foreign communication from a related counterpart application—Russian Office Action with translation dated May 16, 2012, RU2010121135/15(030016), 7 pages.
Foreign communication from a related counterpart application—Second Chinese Office Action with translation dated May 18, 2012, CN200880112983.0, 8 pages.
Foreign communication from a related counterpart application—Ukrainian Office Action with translation dated Jun. 15, 2012, UK2010 06417/(MI-7361), 5 pages.
Foreign communication from the priority application—International Preliminary Report on Patentability, PCT/PT2008/000043, Apr. 27, 2010, 7 pages.
Foreign communication from the priority application—International Search Report and Written Opinion, PCT/PT2008/000043, Jan. 30, 2009, 12 pages.
Hancock, Bruno C., et al. "The Relative Densities of Pharmaceutical Powders, Blends, Dry Granulations, and Immediate-Release Tablets," Pharmaceutical Technology. Apr. 2003, pp. 64-80 (even number pages only due to publication error).
Khattab, Ibrahim, et al., "Effect of Mode of Incorporation of Disintegrants in the Characteristics of Fluid-bed Wet-granulated Tablets," J. Pharm. Pharmacol., 1993, vol. 45, pp. 687-691.
Remington: The Science and Practice of Pharmacy. 21st Edition (2005) pp. 896-900.
Remington: The Science and Practice of Pharmacy 21st Edition (2005) pp. 932-933.
Foreign communication from a related counterpart application—Russian Office Action with translation issued May 27, 2013, RU2010121135/15(030016), 7 pages.
Foreign Communication from a related counterpart application—Japanese Final Office Action with translation, JP Application No. 2010-530951, issued Mar. 11, 2014, 8 pages.
Foreign communication from a related counterpart application—Belarus Office Action with translation issued Jan. 21, 2014, Application No. 20100817. 7 pages.
Australian Office Action issued Oct. 13, 2014, Application No. 2008317584.
Russian Office Action issued Jul. 9, 2014, Application No. 2010121135/15(030016).
Translation of Russian Office Action with translation issued Jul. 9, 2014, Application No. 2010121135/15(030016).
Office Action from Japanese Patent Office dated Jun. 27, 2015, issued in Japanese Patent Application No. 2014-141894 (4 pages).
Translation of Office Action from Japanese Patent Office dated Jun. 27, 2015, issued in Japanese Patent Application No. 2014-141894.(4 pages).
Pharmaceutical Engineering, Chijin Shokan Co., Ltd., 1971 (pp. 174-176).
Translation of relevant parts of Pharmaceutical Engineering, Chijin Shokan Co., Ltd., 1971 (pp. 174-176).
Makoto Otsuka et al., "Effect of Polymorphic Forms of Bulk Powders on Pharmaceutical Properties of Carbamazephine Granules," 47(6) Chem. Pharm. Bull. 852-856 (1999).
Japanese Office Action issued in the corresponding Japanese Patent Application No. 2014-141894.
Lamba et al., 2016. Extended-Release Once-Daily Formulation of Tofacitinib: Evaluation of Pharmacokinetics Compared With Immediate-Release Tofacitinib and Impact of Food. J Clin Pharmacol. Mar. 11, 2016. doi: 10.1002/jcph.734.
Peltola et al., 2015. Practical guidance and considerations for transitioning patients from oxcarbazepine or carbamazepine to eslicarbazepine acetate—Expert opinion, Epilepsy & Behavior 50: 46-49.

* cited by examiner

PHARMACEUTICAL COMPOSITION COMPRISING LICARBAZEPINE ACETATE

CROSS-REFERENCE TO RELATED APPLICATIONS

This application is a continuation of U.S. application Ser. No. 13/754,439 filed on Jan. 30, 2013, now abandoned, which is a continuation of U.S. application Ser. No. 12/257,240, filed Oct. 23, 2008, now U.S. Pat. No. 8,372,431, issued on Feb. 12, 2013, which claims the benefit of U.S. Provisional Application No. 60/982,790, filed on Oct. 26, 2007. The contents of these applications are each incorporated herein by reference.

BACKGROUND OF THE INVENTION

This invention relates to pharmaceutical compositions and methods of making them. More specifically the invention relates to pharmaceutical compositions containing licarbazepine acetate, especially eslicarbazepine acetate.

Eslicarbazepine acetate is a voltage-gated sodium channel (VGSC) blocker suitable for use as an anticonvulsant for example in treating epilepsy, affective disorders and neuropathic pain.

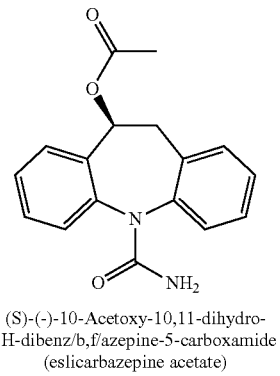

(S)-(-)-10-Acetoxy-10,11-dihydro-
5H-dibenz/b,f/azepine-5-carboxamide
(eslicarbazepine acetate)

This molecule is structurally related to carbamazepine and oxcarbazepine, but has been specifically designed to reduce the production of toxic metabolites (such as epoxides) and to avoid enantiomeric impurity, and the unnecessary production of enantiomers or diastereoisomers of metabolites and conjugates, without losing pharmacological activity. It shares with carbamazepine and oxcarbazepine the dibenzazepine nucleus bearing the 5-carboxamide substitute but is differs at the 10,11-position. This molecular variation results in differences in metabolism, preventing the formation of toxic epoxide metabolites, such as carbamazepine-10,11 epoxide.

SUMMARY OF THE INVENTION

Broadly, the present invention relates to a pharmaceutical composition containing licarbazepine acetate, preferably eslicarbazepine acetate, in combination with at least one pharmaceutically acceptable excipient. The invention also relates to methods of making a pharmaceutical composition containing licarbazepine acetate, preferably eslicarbazepine acetate. The at least one excipient may include conventional excipients, such as one or more diluents/fillers, binders, disintegrants, glidants and lubricants. As used herein the term 'composition' is used interchangeably with the term 'formulation' and is intended to refer to the final oral dosage form such as a tablet or capsule.

According to one aspect of the invention, a pharmaceutical composition is provided wherein the composition comprises licarbazepine acetate, preferably eslicarbazepine acetate, in combination with a binder and a disintegrant, wherein the composition comprises granules of the licarbazepine acetate, and wherein at least part of the disintegrant is present in the granules (intragranular) and at least part of the disintegrant is extragranular.

According to another aspect, the present invention provides a pharmaceutical composition, in the form of an oral dosage form, comprising licarbazepine acetate, preferably eslicarbazepine acetate, wherein the composition does not contain any filler.

In accordance with another aspect of the invention, there is provided a pharmaceutical composition containing licarbazepine acetate, preferably eslicarbazepine acetate, in combination with at least one pharmaceutically acceptable excipient, wherein the composition does not include a wetting agent (i.e. there is no wetting agent at all in the composition).

The present invention results in a large increase in the bulk density: from about 0.28 g/mL in the API prior to granulation to, for example, around 0.6 g/mL in the mixture of drug and excipients (i.e. the preparation) prior to forming the final formulation, for example by compression to form a tablet or by capsule filling. Accordingly, another aspect of the present invention provides a pharmaceutical preparation, wherein the preparation comprises licarbazepine acetate, preferably eslicarbazepine acetate, in combination with a binder and a disintegrant, wherein the bulk density of the preparation is at least about 0.3 g/mL. In the preparation the licarbazepine acetate and part of the disintegrant are preferably present in granules whereas the remaining part of the disintegrant is extragranular. The preparation may further comprise extragranular lubricant. Other excipients may also be present as described in the Detailed Description below.

Preferably the preparation is formed into an oral dosage form, for example by compression to form a tablet.

Preferably the bulk density of the preparation is at least about 0.35 g/mL, more preferably about 0.40 g/mL, even more preferably about 0.45 g/mL, still more preferably about 0.50 g/mL, yet more preferably about 0.55 g/mL. Most preferably the bulk density of the preparation is at least about 0.60 g/mL.

The preparation may be used to form a pharmaceutical composition. In some embodiments, the pharmaceutical composition can be in the form of a solid oral dosage form, such as a tablet or capsule.

Another aspect of the present invention provides a capsule formulation, said formulation comprising a preparation as described above contained in a capsule. The present invention also provides a tablet formulation, said formulation comprising a preparation as described above compressed into a tablet form.

As a result of the improvement in bulk density the inventors have managed to reduce the size and apparent density of compressed formulations such as tablets. According to a another aspect of the invention, a compressed formulation is provided, preferably a tablet, wherein the formulation comprises licarbazepine acetate, preferably eslicarbazepine acetate, in combination with a binder and a disintegrant, wherein the formulation has an apparent density of about 0.5 to about 1.5 g/mL.

Preferably the apparent density of the formulation is about 0.6 to about 1.4 g/mL, more preferably about 0.7 to about 1.3 g/mL, most preferably about 0.8 to about 1.2 g/mL.

Preferably the formulation is comprised of granules, wherein the licarbazepine acetate is intragranular. Preferably the formulation also comprises a disintegrant and a binder. More preferably part of the disintegrant is present in the granules and the remaining part is extragranular. Other excipients may also be present as described in the Detailed Description below.

It has also been found that the use of a granulation process to produce the pharmaceutical composition according to the invention, rather than a direct compression process, results in improved flow and compressibility properties of the licarbazepine acetate. Both wet and dry granulation processes improved compressibility. However, unexpectedly, when the granulation process was scaled up to an industrial scale, the flowability of the licarbazepine acetate was unsatisfactory when using the dry granulation method; only the wet granulation process improved flowability.

Thus, according to another aspect of the invention there is provided a process for preparing a pharmaceutical composition, preferably an oral dosage form, comprising the following steps: mixing licarbazepine acetate, preferably eslicarbazepine acetate, with a pharmaceutically acceptable granulation liquid, and optionally with one or more excipients; granulating the eslicarbazepine acetate and the granulation liquid; optionally mixing the granules with one or more suitable excipients to form a preparation; and forming an oral dosage form.

The optional excipients can be one or more selected from binder, filler/diluent, disintegrant, lubricant and glidant.

In a preferred embodiment, the granulation step also comprises drying the licarbazepine acetate and granulation liquid mixture.

Although the wet granulation process is effective to solve the flowability problems associated with direct compression, there can be problems with binding when the process is scaled up to an industrial scale. It has been found that these problems can be solved by using a wet granulation process in which part of the binder is mixed with the licarbazepine acetate, for example in a powder form, and the remaining part is present in the granulation liquid.

Accordingly, another aspect of the present invention provides a process for preparing a pharmaceutical composition, preferably an oral dosage form, comprising the steps of: mixing licarbazepine acetate, preferably eslicarbazepine acetate, with at least one excipient including part of the total amount of binder; providing a granulation liquid; dissolving or dispersing the remaining proportion of the total amount of the binder in the granulation liquid; granulating the mixture from the mixing step using the granulation liquid produced in the dissolving or dispersing step to produce granules; and optionally forming an oral dosage form.

The process may comprise an additional step involving contacting the granules with one or more suitable excipients, for example, prior to forming the oral dosage form.

Preferably the licarbazepine acetate is mixed with about 20 to about 80 wt % (with respect to the total weight of the composition) binder, more preferably about 20 to about 80 wt % binder, even more preferably about 40 to about 70 wt % binder, most preferably about 30 to about 70 wt % binder, whilst the remainder of the binder is dissolved or dispersed in the granulation liquid, for example about 20 to about 80 wt % of the total weight of the binder may be present in the granulation liquid.

Preferably the binder mixed with the licarbazepine acetate is in the form of a powder, preferably a dry powder. A dry powder as used herein has a liquid (e.g. water) content of less than about 15%.

Preferably the one or more suitable excipients includes a disintegrant. Preferably the one or more excipients includes a lubricant. Additional excipients may include one or more of diluent/filler, glidant, sweetener, and flavouring.

In a more preferred embodiment a portion of the disintegrant is mixed with the licarbazepine acetate prior to the granulating step and the remaining portion is contacted with the granules prior to forming the dosage form.

Where a sweetener is to be used, it is preferred that the sweetener is mixed with the licarbazepine acetate, prior to mixing with the granulation liquid (i.e. the sweetener is intended to be intragranular).

Where a flavouring agent is to be used, it is preferred that the flavouring agent is mixed with the licarbazepine acetate granules formed in the granulation step (i.e. the flavouring agent is intended to be extragranular).

Suitable granulation liquids include water, a lower alcohol such as ethanol or a mixture thereof.

Preferably the process further involves a drying step, in particular the granules may be dried following the granulation step. The drying step may also be followed by a screening step wherein the granules are screened for example, by size or shape.

Preferably the oral dosage form is a tablet. In this embodiment, forming the oral dosage form involves compressing the mixture of granules and excipient(s).

Alternatively the oral dosage form is a capsular form and the forming step involves filling a suitable capsule with the granules and/or excipients.

DETAILED DESCRIPTION OF THE INVENTION

In terms of physical properties, eslicarbazepine acetate shows marked differences to carbamazepine and oxcarbazepine, resulting in different challenges for the galenical chemist. For example, oxcarbazepine, carbamazepine and eslicarbazepine acetate have different crystal forms and in fact, carbamazepine and oxcarbazepine each show several different crystal forms. Drugs with different crystal forms present differences in dissolution, particle size, bulk density and flow properties, all characteristics which influence the formulation process. For example, differences in drugs' crystal shape and in the size of drug particles affect the drugs' relative solubility and dissolution rates, presenting new challenges to the formulation chemist, particularly in terms of disintegration of the formulation. Crystal form and particle size also affect cohesiveness of the particles which in turn affects formation of tablets and binding of particles during granulation.

Licarbazepine acetate is optically active, existing in two enantiomeric forms. In this specification the expression 'licarbazepine acetate' encompasses the individual R- and S-isomers, the racemic mixture of the isomers, and also non-racemic mixtures of the R- and S-isomers in any proportion. In this specification "R-licarbazepine acetate" means the R-isomer in substantially pure form, i.e., at least about 90% pure, preferably at least about 95% pure, more preferably at least about 98% pure, and most preferably at least about 99% pure. In this specification "eslicarbazepine acetate" or "S-licarbazepine acetate" means the S-isomer in substantially pure form, i.e., at least about 90% pure, preferably at least about 95% pure, more preferably at least about 98% pure, and most preferably at least about 99% pure.

Further description of licarbazepine acetate, methods of manufacture, and some of its uses are described in U.S. Pat. Nos. 5,753,646, 7,119,197, 7,241,886, 7,189,846, U.S. Publication No. 20080081930, WO2006/005951, US Publication No. 20080139807, US Publication No. 20060252745, US Publication No. 20060252746, WO2007/012793, WO2007/094694, and WO2007/117166, which are incorporated herein by reference in their entirety.

Certain physical properties of licarbazepine acetate cause problems for its formulation on large-scale, in particular for formation of a tablet formulation, which is preferred for reasons of ease of administration and dosage control. The compound has extremely low bulk density (less than about 0.3 g/mL). This low bulk density means that the compound exhibits poor flowability and can be therefore difficult to handle, particularly on an industrial scale. Moreover, the compound can be difficult to compress and results in very large tablet sizes. The tablets can also show very poor dissolution.

The inventors were able to improve dissolution on a laboratory scale by adding a disintegrant prior to granulating the eslicarbazepine acetate. However, they surprisingly discovered that when part of the disintegrant was added to the mixture after granulating, the dissolution was improved.

In order to reduce the tablet size, the amount of filler can be reduced or eliminated. Substances acting as fillers often have additional effects such as binding, which may lead to unsatisfactory binding and consequent poor technological properties, such as hardness or friability.

Binders generally function more effectively when they are used as liquids or dispersions. However, the inventors found that the problems described above could be solved by preparing the tablet using a wet granulation process in particular, one in which part of the binder is dissolved or dispersed in the granulation liquid, and the rest of the binder is added as a powder with the licarbazepine acetate. Surprisingly, the bulk density of the granulate produced from this mixture was more than double that of the raw drug material prior to granulation.

Additionally, in another aspect, the present invention discloses that inclusion of part of the disintegrant intragranular and part extragranular improved dissolution.

Dosage Form

Preferably the composition is an oral dosage form, more preferably a solid oral dosage form such as a capsule or a tablet. Preferably the solid oral dosage form is a tablet. The tablet can be coated.

Disintegrant

A disintegrant is a substance which helps the composition break up once ingested. Preferably the total weight of the composition is comprised of about 0.5 to about 70 wt % disintegrant, more preferably about 0.5 to about 20 wt % disintegrant, more preferably about 3 to about 15 wt % disintegrant, about 2 to about 15 wt %, or about 2 to about 8 wt %.

About 0 to about 100 wt % of the total amount of the disintegrant can be present in the granules. More preferably, about 20 to about 80 wt % of the total amount of the disintegrant is present in the granules. More preferably about 30 to about 70 wt % of the total amount of the disintegrant is present in the granules. More preferably about 40 to about 60 wt % of the total amount of the disintegrant is present in the granules. More preferably about 45 to about 55 wt % of the total amount of the disintegrant is present in the granules. Most preferably about 50 wt % of the total amount of the disintegrant is present in the granules. The remaining proportion of the disintegrant is preferably present extragranular.

In a most preferred embodiment, the disintegrant is present both in the granules and extragranular.

Suitable disintegrants include alginic acid (Kelacid™, Protacid™, Satialgine H8™), calcium phosphate, tribasic (Tri-Cafos™, TRI-CAL WG™, TRI-TAB™), carboxymethylcellulose calcium (ECG 505™, Nymcel ZSC™), carboxymethylcellulose sodium (Akucell™, Aquasorb™, Blanose™, Finnfix™, Nymcel Tylose CB™), colloidal silicon dioxide (Aerosil™, Cab-O-Sil™, Cab-O-Sil M-5P™, Wacker HDK™), croscarmellose sodium (Ac-Di-Sol™, Explocel™, Nymcel ZSX™, Pharmacel XL™, Primellose™, Solutab™, Vivasol™), crospovidone (Kollidon CL™, Kollidon CL-M™, Polyplasdone XL™, Polyplasdone XL-IO™), docusate sodium, guar gum (Galactosol™, Meprogat™, Meyprodor™, Meyprofin™, Meyproguar™), low substituted hydroxypropyl cellulose, magnesium aluminum silicate (Carrisorb™, Gelsorb™, Magnabite™, Neusilin™, Pharmsorb™, Veegum™), methylcellulose (Benecel™, Culminal MC™, Methocel™, Metolose™), microcrystalline cellulose (Avicel PH™, Celex™, Celphere™, Ceolus KG™, Emcoel™, Ethispheres™, Fibrocel™, Pharmacel™, Tabulose™, Vivapur™), povidone (Kollidon™, Plasdone™) sodium alginate (Kelcosol™, Keltone™, Protanal™), sodium starch glycolate (Explotab™, Primojel™, Vivastar P™), polacrilin potassium (Amberlite IRP88™), silicified microcrystalline cellulose (ProSolv™), starch (Aytex P™, Fluftex W™, Instant PureCote™, Melojel™, Meritena™, Paygel 55™, Perfectamyl D6PH™, Pure-Bind™, Pure-Cote™, Pure-Dent™, Pure-Gel™, Pure-Set™, Purity 21™, Purity 826™, Tablet White™) or pre-gelatinized starch (Instanstarch™, Lycatab C™, Lycatab PGS™, Merigel™, National 78-1551™, Pharma-Gel™, Prejel™, Sepistab ST 200™, Spress B820™, Starch 1500 G™, Tablitz™, Unipure LD™ and Unipure WG220™), or mixtures thereof.

Preferred disintegrants are super-disintegrants such as croscarmellose sodium, crospovidone, low substituted hydroxypropyl cellulose, microcrystalline cellulose, carboxymethylcellulose sodium, carboxymethylcellulose calcium and sodium starch glycolate. A particularly suitable disintegrant is croscarmellose sodium. When the disintegrant is croscarmellose sodium, the total weight of the composition is preferably comprised of about 0.5 to about 20 wt %, more preferably about 2 to about 15 wt %, most preferably about 3 to about 15 wt % disintegrant.

Binder

A binder is a substance which holds the components of the composition together in the required composition form.

Preferably the total weight of the composition is comprised of about 0.5 to about 70 wt % binder, more preferably about 0.5 to about 20 wt %, more preferably about 1 to about 14 wt %, still more preferably about 5 to about 9 wt % binder.

Suitable binders for inclusion in the composition of the invention include acacia, alginic acid (Kelacid™, Protacid™, Satialgine H8™), carbomer (Acritamer™, Carbopol™, Pemulen™, Ultrez™), carboxymethylcellulose sodium (Akucell™, Aquasorb™, Blanose™, Finnfix™, Nymcel™, Tylose™), ceratonia (Meyprofleur™), cottonseed oil, dextrin (Avedex™, Caloreen™, Crystal Gum™, Primogran W™), dextrose (Caridex™, Dextrofm™, Lycedex PF™, Roferose™, Tabfine D-IOO™), gelatin (Cryogel™, Instagel™, Solugel™), guar gum (Galactosol™, Meprogat™, Meyprodor™, Meyprofm™, Meyproguar™), hydrogenated vegetable oil type I (Akofine™, Lubritab™, Sterotex™, Dynasan P[omicron]O™, Softisan 154™, Hydrocote™, Lipovol™, HS-K™, Sterotex HM™), hydroxyethyl cellulose (Alcoramnosan™, Cellosize™, Idroramnosan™, Liporamnosan™, Natrosol™, Tylose PHA™), hydroxyethylmethyl cellulose (Culminal™, Tylopur MH™, Tylopur MHB™, Tylose MB™, Tylose MH™, Tylose MHB™), hydroxypropyl cellulose (Klucel™, Methocel™, Nisso HPC™), low substituted hydroxypropyl cellulose, hypromellose (Benecel MHPC™, Methocel™, Metolose™, Pharmacoat™, Spectracel 6™, Spectracel 15™, Tylopur™), magnesium aluminium silicate (Carrisorb™, Gelsorb™, Magnabite™, Neusilin™, Pharmsorb™, Veegum™), maltodextrin (C*Dry MD™, Glucidex™, Glucodry™, Lycatab DSH™, Maldex™, Maltagran™, Maltrin™, Maltrin QD™, Paselli MD 10 PH™, Star-Dri™) maltose (Advantose 100™), methylcellulose (Benecel™, Culminal MC™, Methocel™, Metolose™), microcrystalline cellulose (Avicel PH™, Celex™, Celphere™, Ceolus KG™, Emcocel™, Ethispheres™, Fibrocel™, Pharmacel™, Tabulose™, Vivapur™), polydextrose (Litesse™), polyethylene oxide (Polyox™), polymethacrylates (Eastacryl 30D™, Eudragit™, Kollicoat MAE 30D™, Kollicoat MAE 30DP™), povidone (Kollidon™, Plasdone™), sodium alginate (Kelcosol™, Keltone™, Protanal™), starch (Aytex P™, Fluftex W™, Instant Pure-Cote™, Melojel™, Meritena Paygel 55™, Perfectamyl D6PH™, Pure-Bind™, Pure-Cote™, Pure-Dent™, Pure-Gel™, Pure-Set™, Purity 21™, Purity 826™, Tablet White™), pregelatinised starch (Instastarch™, Lycatab C™, Lycatab PGS™, Merigel™, National 78-1551™, Pharma-Gel™, Prejel™, Sepistab ST 200™, Spress B820™, Starch 1500 G™, Tablitz™, Unipure LD™, Unipure WG 220™), stearic acid (Crodacid™, Emersol Hystrene™, Industrene™, Kortacid 1895™, Pristerene™), sucrose and zein, or mixtures thereof.

Preferred binders include povidone, hypromellose, hydroxypropyl cellulose, methyl-cellulose, ethyl-cellulose, pregelatinised maize starch and gelatine. The most preferred binder is povidone. When the binder is povidone, the total weight of the composition is preferably comprised of about 0.5 to about 14 wt % binder, preferably about 5 to about 9 wt % binder.

Lubricant

The presence of a lubricant is particularly preferred when the composition is a tablet as lubricants improve the tabletting process. Lubricants prevent composition ingredients from clumping together and from sticking to the tablet punches or capsule filling machine and improve flowability of the composition mixture. Accordingly, the total weight of the composition may also preferably be comprised of about 0.1 to about 10 wt % lubricant, more preferably about 1 to about 3 wt % lubricant.

Suitable lubricants include calcium stearate (HyQual™), glycerine monostearate (Capmul GMS-50™, Cutina GMS™, Imwitor™ 191 and 900, Kessco GMS5™ Lipo GMS™ 410, 450 and 600, Myvaplex 600P™, Myvatex™, Protachem GMS-450™, Rita GMS™, Stepan GMS™, Tegin™, Tegin™ 503 and 515, Tegin 4100™, Tegin M™, Unimate GMS™), glyceryl behenate (Compritol 888 ATO™), glyceryl palmitostearate (Precirol ATO 5™), hydrogenated castor oil (Castorwax™, Castorwax MP 70™, Castorwax MP 80™, Croduret™, Cutina HR™, Fancol™, Simulsol 1293™), hydrogenated vegetable oil type I (Akofine™, Lubritab™, Sterotex™, Dynasan P60™, Softisan 154™, Hydrocote™, Lipovol HS-K™, Sterotex HM™), magnesium lauryl sulphate, magnesium stearate, medium-chain triglycerides (Captex 300™, Captex 355™, Crodamol GTC/C™, Labrafac CC™, Miglyol 810™, Miglyol 812™, Myritol™, Neobee M5™, Nesatol™, Waglinol 3/9280™), poloxamer (Lutrol™, Monolan™, Pluronic™, Synperonic™), polyethylene glycol (Carbowax™, Carbowax Sentry™, Lipo™, Lipoxol™, Lutrol E™, Pluriol E™), sodium benzoate (Antimol™), sodium chloride (Alberger™), sodium lauryl sulphate (Elfan 240™, Texapon Kl 21™), sodium stearyl fumarate (Pruv™), stearic acid (Crodacid E570™, Emersol™, Hystrene™, Industrene™, Kortacid 1895™, Pristerene™), talc (Altaic™, Luzenac™, Luzenac Pharma™, Magsil Osmanthus™, Magsil Star™, Superiore™), sucrose stearate (Surfhope SE Pharma D-1803 F™) and zinc stearate (HyQual™), or mixtures thereof.

Preferred lubricants include magnesium stearate and/or sodium lauryl sulphate. In a most preferred embodiment the lubricant is magnesium stearate.

Glidant

Glidants improve the flowability of the composition. The composition may also comprise a glidant. Preferably, the total weight of the composition is comprised of about 0 to about 10 wt %. glidant.

Suitable glidants include tribasic calcium phosphate (Tri-Cafos™, TRI-CAL™, TRI-TAB™), calcium silicate, cellulose, powdered (Arbocel™, Elcema™, Sanacel™, Solka-Floc™), colloidal silicon dioxide (Aerosil™, Cab-O-Sil™, Cab-O-Sil M-5P™, Wacker HDK™), magnesium silicate, magnesium trisilicate, starch (Aytex P™, Fluftex W™, Instant Pure-Cote™, Melojel™, Meritena™, Paygel 55™, Perfectamyl D6PH™, Pure-Bind™, Pure-Cote™, Pure-Dent™, Pure-Gel™, Pure-Set™, Purity 21™, Purity 826™, Tablet White™) and talc (Altaic™, Luzenac™, Luzenac Pharma™, Magsil Osmanthus™, Magsil Star™, Superiore™), or mixtures thereof.

Preferred glidants are colloidal silicon dioxide and/or talc.

Diluent/Filler

The term 'filler' and the term 'diluent' are herein used interchangeably. It is known that, in general, the term 'filler' is used in the context of capsular formulations and the term 'diluent' in tablet formulations. Fillers fill out the size of a composition, making it practical to produce and convenient for the consumer to use.

The composition may comprise a diluent/filler, which may be present in an amount up to about 70 wt % of the total weight of the composition.

When present in the composition, suitable fillers include for example calcium carbonate (Barcroft™, Cal-Carb™, CalciPure™, Destab™, MagGran™, Millicarb™, Pharma-Carb™, Precarb™, Sturcal™, Vivapres Ca™), calcium phosphate, dibasic anhydrous (A-TAB™, Di-Cafos A-N™, Emcompress Anhydrous™, Fujicalin™), calcium phosphate, dibasic dihydrate (Cafos™, Calipharm™, Calstar™, Di-Cafos™, Emcompress™), calcium phosphate tribasic (Tri-Cafos™, TRI-CAL WG™, TRI-TAB™), calcium sulphate (Destab™, Drierite™, Snow White™, Cal-Tab™, Compactrol™, USG Terra Alba™), cellulose powdered (Arbocel™, Elcema™, Sanacel™, Solka-Floc™), silicified microcrystalline cellulose (ProSolv™), cellulose acetate, compressible sugar (Di-Pac™), confectioner's sugar, dextranes (Candex™, Emdex™), dextrin (Avedex™, Caloreen™, Crystal Gum™, Primogran W™), dextrose (Caridex™, Dextrofin™, Lycadex PF™, Roferose™, Tab fine D-IOO™), fructose (Advantose™, Fructamyl™, Fructofin™, Krystar™), kaolin (Lion™, Sim 90™), lactitol (Finlac ACX™, Finlac DC™, Finlac MCX™), lactose (Aero Flo 20™, Aero Flo 65™, Anhydrox™, CapsuLac™, Fast-Flo™, FlowLac™, GranuLac™, InhaLac™, Lactochem™, Lactohale™, Lactopress™, Microfine™, Microtose™, Pharmatose™, Prisma Lac™, Respitose™, SacheLac™, SorboLac™, Super-Tab™, Tablettose™, Wyndale™, Zeparox™), magnesium carbonate, magnesium oxide (MagGran MO™), maltodextrin (C*Dry MD™, Glucidex™, Glucodry™, Lycatab DSH™, Maldex™, Maltagran™, Maltrin™, Maltrin QD™, Paselli MD 10 PH™, Star-Dri™), maltose (Advantose 100™), mannitol (Mannogem™, Pearlitol™), microcrystalline cellulose (Avicel PH™, Celex™, Celphere™, Ceolus KG™, Emcocel™, Ethispheres™, Fibrocel™, Pharmacel™, Tabulose™, Vivapur™), polydextrose (Litesse™), simethicone (Dow Corning Q7-2243 LVA™, Cow Corning Q7-2587™, Sentry Simethicone™), sodium alginate (Kelcosol™, Keltone™, Protanal™), sodium chloride (Alberger™), sorbitol (Liponec 70-NC™, Liponic 76-NCv, Meritol™, Neosorb™, Sorbifin™, Sorbitol Instant™, Sorbogem™), starch (Aytex P™, Fluftex W™, Instant Pure-Cote™, Melojel™, Meritena Paygel 55™, Perfectamyl D6PH™, Pure-Bind™, Pure-Cote™, Pure-Dent™, Pure-Gel™, Pure-Set™, Purity 21™, Purity 826™, Tablet White™), pregelatinized starch (Instastarch™, Lycatab C™, Lycatab PGS™, Merigel™, National 78-1551™, Pharma-Gel™, Prejel™, Sepistab ST 200™, Spress B820™, Starch 1500 G™, Tablitz™, Unipure LD™, Unipure WG220™), sucrose, trehalose and xylitol (Klinit™, Xylifm™, Xylitab™, Xylisorb™, Xylitolo™), or mixtures thereof.

The diluent/filler is preferably selected from calcium phosphate, dibasic dehydrate, microcrystalline cellulose or lactose. Alternatively, any suitable diluent/filler can be used.

However, in a most preferred embodiment, the composition does not contain any filler/diluent.

Flavouring/Sweetening Agent

In an embodiment, the composition further includes a flavouring and/or a sweetening agent, each of which may be present in an amount of about 0.1 to about 2 wt % of the total weight of the composition.

The presence of these excipients is particularly desirable in paediatric compositions. Suitable flavouring agents include chocolate, bubble gum, cocoa, coffee, fruit flavouring (such as wild cherry, banana, grape, peach, and, raspberry), oil of peppermint, oil of spearmint, oil of orange, mint flavour, anise flavour, honey flavour, vanilla flavour, tea flavour and verbena flavour, and various fruit acids such as citric acid, ascorbic acid and tartaric acid, or mixtures thereof.

The raspberry flavour and the banana flavour have been found to yield particularly palatable products. When the flavouring agent is banana flavour, the total weight of the composition is comprised of about 0.1 to about 3 wt % flavouring agent.

Preferably about 30 to about 100 wt %, more preferably about 60 to about 100 wt %, even more preferably about 80 to about 100 wt % of the total amount of the flavouring agent is present extra-granular. The remaining proportion of flavouring agent is intragranular. Preferably either all or the majority (at least about 50 wt %) of the flavouring agent is extragranular.

Suitable sweetening agent(s) is (are) selected from gluconate, aspartame, cyclamate, sodium saccharine, xylitol and maltitol, or mixtures thereof. Preferably, the sweetening agent is aspartame or sodium saccharine. When the sweetening agent is sodium saccharine, the total weight of the composition is comprised of about 0.1 to about 5 wt % sweetening agent.

Preferably about 20 to about 100 wt % of the total amount of the sweetening agent is intragranular. More preferably, about 50 to about 100 wt % of the total amount of the sweetening agent is intragranular. Most preferably about 80 to about 100 wt % of the total amount of the sweetening agent is present intragranular. The remaining proportion of sweetening agent is extragranular. Preferably either all or the majority (at least about 50 wt %) of the sweetening agent is intragranular.

Wetting Agent

A wetting agent is an excipient that decreases the contact angle of a solid particle in liquid medium, thus improving drug solubility and dissolution in solid formulations.

The composition may optionally further comprise a wetting agent. However, in a preferred embodiment the composition does not contain any wetting agent. In particular the composition does not include any sodium lauryl sulphate.

When present in the composition, suitable wetting agents include for example gelatin, casein, lecithin (phosphatides), gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (also known as polysorbates) (e.g., TWEEN™), polyethylene glycols, polyoxyethylene stearates, phosphates, sodium lauryl sulphate, poloxamer, sodium dodecylsulfate, carboxymethylcellulose calcium, carboxymethylcellulose sodium, methylcellulose, hydroxyethylcellulose, hydroxyl propylcellulose, hydroxypropylmethylcellulose phthalate, noncrystalline cellulose, magnesium aluminum silicate, triethanolamine, polyvinyl alcohol, polyvinylpyrrolidone (also known as PVP), yloxapol (also known as superinone or triton), and combinations thereof.

In general, excipients mixed with the licarbazepine prior to granulation are intragranular and may include one or more of diluent/filler, disintegrant, sweetener, flavouring agent and, binder. Those excipients which are contacted with the granules prior to forming the oral dosage form (i.e. are added after granulation) are, in general, extragranular and include one or more of filler/diluent, disintegrant, lubricant, flavouring agent, sweetener and glidant. In this way excipients can be extra- and/or intragranular.

Density

Preferably the bulk density of the preparation is at least about 0.35 g/mL, more preferably at least about 0.40 g/mL, even more preferably at least about 0.45 g/mL, still more preferably at least about 0.50 g/mL, yet more preferably at least about 0.55 g/mL. Most preferably the bulk density of the preparation is at least about 0.60 g/mL.

Suitable methods for determining the bulk density of the preparation will be well known to the skilled chemist, for example, the European Pharmacopeia edition 6, Test 2.9.15 "apparent volume", pages 285-286, EDQM, 2007, or USP 31, vol. 1 test <616> page 231-232, The United States Pharmacopeia Convention, 2008. The apparent density of a compressed formulation is measured in terms of mass and volume of the formulation and is well within the capabilities of the skilled person.

A suitable method is described below:

Apparatus settling apparatus capable of producing in 1 minute 250±15 taps from a height of 3±0.2 mm. The support for the graduated cylinder with its holder, has a mass of 450±5 g a 250 ml graduated cylinder (2 ml intervals) with a mass of 220±40 g Method Into a dry cylinder, introduce without compacting, 100.0 g (mg) of the test substance. Secure the cylinder in its holder. Read the unsettled apparent volume ($V_0$) to the nearest millilitre. Carry out 10, 500 and 1250 taps and read the corresponding volumes $V_{10}$, $V_{500}$, $V_{1250}$, to the nearest millilitre. If the difference between $V_{500}$ and $V_{1250}$ is greater than 2 ml, carry out another 1250 taps.

Alternatively, if it is not possible to select 100 g, select a test sample of any mass but with a volume between 50 ml and 250 ml, measure its apparent volume, $V_0$ as described above, and weigh the sample and specify the mass in the expression of results.

Bulk/apparent density may then be determined in g/ml using the following formula:

$$m/V_0$$

where m is the mass in grams and $V_0$ the unsettled apparent volume.

Preferred features and embodiments of each aspect of the invention are as for each of the other aspects mutatis mutandis unless the context demands otherwise. For example, the majority of preferred features are applicable both to tablet and to capsular dosage forms.

EXAMPLES

The invention will be further described with reference to the following examples.

Exemplary Compositions

Example 1

| | |
|---|---|
| Eslicarbazepine acetate | 55-60% |
| Diluent | 30-40% |
| Binder | 4-6% |
| Disintegrant | 6-8% |
| Lubricant | 0.5-1.5% |

Example 2

| | |
|---|---|
| Eslicarbazepine acetate | 70-75% |
| Diluent | 12-16% |
| Binder | 4-6% |
| Disintegrant | 5-7% |
| Lubricant 1 | 0.5-1.5% |
| Lubricant 2 | 0.5-1.5% |

Example 3

| | |
|---|---|
| Eslicarbazepine acetate | 82-89% |
| Binder | 7-9% |
| Disintegrant | 5-7% |
| Flavouring agent | 0.4-0.6% |
| Sweetening agent | 0.6-0.9% |
| Lubricant | 0.5-1.5% |

Example 4

| | |
|---|---|
| Eslicarbazepine acetate | 82-89% |
| Binder | 5-8% |
| Disintegrant | 5-8% |
| Lubricant | 1-3% |

Specific Examples

Example 5

Dry Granulation Formulation

| | |
|---|---|
| Eslicarbazepine acetate | 35-45 wt % |
| Microcrystalline cellulose | 40-60 wt % |
| Croscarmellose sodium (intragranular) | 5-15 wt % |
| Magnesium stearate | 0.3-2.0 wt % |
| Talc | 1.0-wt 5% |
| Magnesium stearate | 0.1-wt 2.0% |

Example 6

Wet Granulation Formulation (i)

| | |
|---|---|
| Eslicarbazepine acetate(intragranular) | 5-70 wt % |
| Emcompress ® (intragranular) | 20-85 wt % |
| Povidone | 1-10 wt % |
| Croscarmellose sodium (½ intra-/½ extragranular) | 1-10 wt % |
| Ethanol 96% | q. ad. |
| Magnesium stearate (extragranular) | 0.1-2.5 wt % |

Example 7

Wet Granulation Formulation (ii)

| | |
|---|---|
| Eslicarbazepine acetate (intragranular) | 65-85 wt % |
| Emcompress ® (intragranular) | 10-30 wt % |
| Povidone (½ powder/½ dispersion) | 1-10 wt % |
| Croscarmellose sodium (½ intra-/½ extragranular) | 1-10 wt % |
| Ethanol 96% | q. ad. |
| Magnesium stearate (extragranular) | 0.1-2.5 wt % |
| Sodium Lauryl sulphate (extragranular) | 0.1-2.5 wt % |

Example 8

Wet Granulation Formulation (iii)

| | |
|---|---|
| Eslicarbazepine acetate (intragranular) | 65-85 wt % |
| Emcompress ® (intragranular) | 5-30 wt % |
| Microcrystalline cellulose (intragranular) | 5-70 wt % |
| Povidone (100% powder) | 1-10 wt % |
| Croscarmellose sodium (½ intra-/½ extragranular) | 1-10 wt % |
| Ethanol 96% | q. ad. |
| Magnesium stearate (extragranular) | 0.1-2.5 wt % |

Example 9

Formulation with Flavourings and Sweeteners

| | |
|---|---|
| Eslicarbazepine acetate (intragranular) | 70-90 wt % |
| Povidone (½ powder/½ dispersion) | 2-15 wt % |
| Croscarmellose sodium (½ intra-/½ extragranular) | 2-15 wt % |
| Ethanol 96% | q. ad. |
| Magnesium stearate (extragranular) | 0.1-2.5 wt % |
| Banana flavour (extragranular) | 0.1-2.0 wt % |
| Sodium saccharin (intragranular) | 0.1-2.0 wt % |

Example 10

| | |
|---|---|
| Eslicarbazepine acetate (intragranular) | 80-90 wt % |
| Povidone (½ powder/½ dispersion) | 3-10 wt % |
| Croscarmellose sodium (½ intra-/½ extragranular) | 3-10 wt % |

-continued

| | |
|---|---|
| Purified water | q. ad. |
| Magnesium stearate (extragranular) | 0.1-3.0 wt % |

Tablets were made on both small and industrial scale as follows.

Small Scale/semi-industrial

Eslicarbazepine acetate was mixed with half of the binder, povidone, and half of the disintegrant, croscarmellose sodium, in a blender for 10 minutes. The remaining half of the povidone was dispersed in purified water. The eslicarbazepine acetate, povidone-disintegrant mixture was then wet with the purified water before granulation (Ø1.6 mm). The granules were dried on a tray drier with extraction at 50° C. to a moisture content between 1.0-3.0%. The granules were then calibrated. The calibrated granules were added to the other half of the croscarmellose sodium and mixed for 10 minutes in a blender. The lubricant, magnesium stearate, was added and the final mixture mixed for 5 minutes before compression into tablets.

Industrial Scale

Eslicarbazepine acetate, half of the binder, povidone, and half of the disintegrant, croscarmellose sodium, were added to a high shear mixer/granulator. The remaining povidone was dispersed in the granulation fluid (water) and added to the granulator for wet granulation. The granules formed were unloaded and dried on a fluid bed drier at 66° C. the granules to a moisture content of between 1.0-3.0%). The dried granules were then calibrated (Ø1.0 mm). The calibrated granules were added the other half of croscarmellose sodium and mixed for 10 minutes in a blender. The lubricant, magnesium stearate, was added and the final mixture mixed for 5 minutes, before compression into tablets.

Comparison of Tablet Characteristics after Wet and Dry Granulation

Composition and Manufacturing Process for Wet and Dry Granulation Experiments

| Starting materials | Quantity (mg/tablet) | Function | Manufacturing process |
|---|---|---|---|
| Eslicarbazepine acetate | 600.0 | Active substance | Wet granulation process |
| Emcompress® | 300.0 | Diluent | Blend eslicarbazepine acetate, emcompress, povidone and ½ croscarmellose sodium in a suitable blender, for |
| Povidone | 50.0 | Binder | 10 minutes at 25 r.p.m. |
| | | | Wet the mixture with ethanol. Granulate. Dry (40° C.) |
| Croscarmellose sodium | 70.0 | Disintegrant | and calibrate through a Ø 1.0 mm sieve. |
| | | | Add the remaining croscarmellose sodium and blend |
| Magnesium stearate | 10.0 | Lubricant | for 10 min. at 25 r.p.m. |
| | | | Add magnesium stearate to the previous mixture and |
| Final tablet weight | 1030 | | blend for 5 more minutes at 25 r.p.m. |
| | | | Compress the final mixture using oblong punches |
| | | | Dry granulation process |
| | | | Blend eslicarbazepine acetate, emcompress, povidone and ½ croscarmellose sodium in a suitable blender, for 10 minutes at 25 r.p.m |
| | | | Add ½ of magnesium stearate to the mixture and blend for 5 min. at 25 r.p.m. |
| | | | Compress the mixture without control of the weight and hardness of the tablets obtained. |
| | | | Break the tablets in a suitable granulator and pass the obtained granules primarelly in a Ø 1.6 mm sieve and then through a Ø 1.0 mm sieve. |
| | | | Add the remaining croscarmellose sodium and blend for 10 minutes at 25 r.p.m. Add the second portion of magnesium stearate and mix for 5 minutes at 25 r.p.m. Compress the final mixture using oblong punches. |

Results

| Batch | Wet | Dry | Method |
|---|---|---|---|
| Bulk density (g/ml) | 0.49 | 0.58 | Ph. Eur. edn. 6, test 2.9.15 or USP 31 <616> |
| Compressibility index (%) | 11.3 | 18.9 | Ph. Eur. edn. 6, 2.9.15 or USP 31 <616> |
| Flow rate (g/s) | 17 | No flow | Ph. Eur. edn. 6, 2.9.16 or USP 31 <1174> |
| strength | 600 | 600 | N/A |
| Average weight (mg) | 1022 | 1021 | Ph. Eur. edn. 6, 2.9.5 |
| Thickness (mm) | 5.7 | 6.2 | The thickness of 10 tablets was measured with a gauge and the average determined. |
| Friability (%) | 0.08 | 4 broken tablets | Ph. Eur. edn. 6, 2.9.7 or USP 31 <1216> |
| Hardness (Kp) | 27.5 | 9.9 | Ph. Eur. edn. 6, 2.9.8 or USP 31 <1217> |

-continued

| Batch | Wet | Dry | Method |
|---|---|---|---|
| Dissolution 30'(%) | 81.5 | 67.9 | Ph. Eur. edn. 6, 2.9.3 or USP 31 <711>; the paddle apparatus was used at 100 rpm in pH 4.5 |

These results show the advantages gained by using wet rather than dry granulation, notably in the flowability, compressability fields and tablet properties.

Effect of Binder Addition on Granule Characteristics on Lab Scale and on Industrial Scale

| Batch | Lab-scale | Lab-scale | Lab-scale | Industrial Scale | methods |
|---|---|---|---|---|---|
| Binder adding technique | Dry | 50% dry + 50% dispersed | 100% dispersed | 50% dry + 50% dispersed | N/A |
| Bulk density (g/ml) | 0.53 | 0.54 | 0.54 | 0.61 | Ph. Eur. edn. 6, 2.9.15 or USP 31 <616> |
| Compressibility index (%) | 6.2 | 6.7 | 7.1 | 6.3 | Ph. Eur. edn. 6, 2.9.15 or USP 31 <616> |
| Hausner ratio | 1.18 | 1.15 | 1.17 | 1.13 | Ph. Eur. edn. 6, 2.9.15 or USP 31 <616> |
| Flow rate (g/ml) | 18.3 | 18.6 | 18.9 | 20.2 | Ph. Eur. edn. 6, 2.9.16 or USP 31 <1174> |
| Porosity (%) ([1-(bulk density/real density)] × 100) | 61.9 | 61.3 | 61.3 | 56.1 | Bulk density was determined by Ph. Eur. edn. 6, 2.9.15 or USP 31 <616>; Real density was determined by Ph. Eur. edn. 6, 2.9.23 or USP 31 <699> (gas pycnometry) |

These results show that the method of addition of the binder, whilst not having a significant effect at laboratory scale, showed great improvements in both flowability and density at industrial scale.

Various modifications to the invention as described herein are within the scope of the invention. The skilled chemist will be aware of how to adjust the proportions of the excipients to achieve the results of the invention within the scope of the claims. While only certain embodiments have been described, it will be understood by those skilled in the art that various changes in form and details may be made therein without departing from the spirit and scope as defined by the appended claims. Those skilled in the art will recognize, or be able to ascertain using no more than routine experimentation, many equivalents to the specific embodiments described specifically herein. Such equivalents are intended to be encompassed in the scope of the appended claims.

All references cited herein are hereby incorporated by reference herein in their entirety.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent or later-developed techniques which would be apparent to one of skill in the art.

As used herein, the recitation of a numerical range is intended to convey that the embodiments may be practised using any of the values within that range, including the bounds of the range. The variable can take multiple values in the range, including any sub-range of values within the cited range.

What is claimed is:

1. A tablet or capsule consisting essentially of:
    a granular phase comprising licarbazepine acetate and a super-disintegrant selected from the group consisting of croscarmellose sodium, crospovidone, sodium starch glycolate, and mixtures thereof;
    an extragranular phase comprising a lubricant and a super-disintegrant selected from the group consisting of croscarmellose sodium, crospovidone, sodium starch glycolate, and mixtures thereof; and
    optionally one or more additional excipients selected from the group consisting of (1) a binder selected from the group consisting of povidone, pregelatinized starch, gelatin, and mixtures thereof, (2) a diluent/filler, (3) a disintegrant, (4) a glidant, (5) a lubricant, and (6) mixtures thereof; and
    wherein the amount of licarbazepine acetate present in the granular phase ranges from 70 to 90 percent by weight relative to the total weight of the tablet or capsule;
    wherein the total amount of super-disintegrant ranges from 5 to 10 percent by weight relative to the total weight of the tablet or capsule; and
    wherein 30 to 70 percent by weight of the total amount of super-disintegrant is present in the granular phase.

2. The tablet or capsule according to claim 1, wherein the licarbazepine acetate is eslicarbazepine acetate.

3. The tablet or capsule according to claim 2, wherein the amount of eslicarbazepine acetate ranges from 80 to 90% by weight relative to the total weight of the tablet or capsule, the amount of povidone ranges from 3 to 10% by weight relative to the total weight of the tablet or capsule, and the amount of croscarmellose sodium ranges from 3 to 10% by weight relative to the total weight of the tablet or capsule.

4. A tablet or capsule comprising:
    a granular phase comprising licarbazepine acetate and a super-disintegrant selected from the group consisting of croscarmellose sodium, crospovidone, sodium starch glycolate, and mixtures thereof;
    an extragranular phase comprising a lubricant and a super-disintegrant selected from the group consisting of croscarmellose sodium, crospovidone, sodium starch glycolate, and mixtures thereof; and
    povidone; and
    wherein the amount of licarbazepine acetate present in the granular phase ranges from 55 to 60 percent by weight relative to the total weight of the tablet or capsule;

wherein the total amount of super-disintegrant ranges from 5 to 10 percent by weight relative to the total weight of the tablet or capsule;
wherein the amount of povidone is 5 to 9 percent by weight relative to the total weight of the tablet or capsule;
wherein 30 to 70 percent by weight of the total amount of super-disintegrant is present in the granular phase; and
wherein the tablet or capsule exhibits a dissolution percentage of 67.9 to 81.5 at 30 minutes when using a paddle apparatus at a speed of 100 rpm under the following combination of conditions: a dissolution medium temperature of 37±0.5° C. and a dissolution medium pH of 4.5.

5. The tablet or capsule according to claim 4, wherein the licarbazepine acetate is eslicarbazepine acetate.

* * * * *